(12) United States Patent
Cameron

(10) Patent No.: US 10,722,107 B2
(45) Date of Patent: Jul. 28, 2020

(54) VIDEO-GUIDED CHEST TUBE INSERTION SYSTEM

(71) Applicant: THE REGENTS OF THE UNIVERSITY OF CALIFORNIA, Oakland, CA (US)

(72) Inventor: Robert Cameron, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 572 days.

(21) Appl. No.: 14/731,697

(22) Filed: Jun. 5, 2015

(65) Prior Publication Data

US 2015/0342699 A1    Dec. 3, 2015

Related U.S. Application Data

(63) Continuation of application No. PCT/US2013/074213, filed on Dec. 10, 2013.
(Continued)

(51) Int. Cl.
*A61B 1/06* (2006.01)
*A61M 27/00* (2006.01)
(Continued)

(52) U.S. Cl.
CPC ............ *A61B 1/0676* (2013.01); *A61B 1/015* (2013.01); *A61B 1/04* (2013.01); *A61B 1/3132* (2013.01); *A61B 17/3415* (2013.01); *A61B 34/20* (2016.02); *A61M 27/00* (2013.01); *A61M 39/0247* (2013.01); *A61B 2034/2057* (2016.02); *A61B 2090/306* (2016.02);
(Continued)

(58) Field of Classification Search
None
See application file for complete search history.

(56) References Cited

U.S. PATENT DOCUMENTS 5,573,531 A    11/1996    Gregory
5,676,151 A    10/1997    Yock
(Continued)

OTHER PUBLICATIONS

Korean Intellectual Property Office (KIPO), International Search Report and Written Opinion, PCT/US2013/074213, Mar. 7, 2014, pp. 1-14, including claims searched, pp. 15-19, counterpart to U.S. Appl. No. 14/731,697 herein.

*Primary Examiner* — Katherine L Fernandez
(74) *Attorney, Agent, or Firm* — O'Banion & Ritchey LLP; John P. O'Banion

(57) ABSTRACT

A chest tube placement apparatus is provided that has an elongate body with a rigid tip that is disposed within the interior of a flexible chest tube and an inflatable member mounted to the body is inflated and the apparatus is then inserted in a prepared location in the chest wall of a patient. The body of the apparatus has at least one axial material transfer channel with a tip port that permits the injection of anesthetic or the aspiration of gases or liquids at the tip. The body also has a light and video camera and display to allow the visualization of the internal structures of the patient during chest tube placement. Once placed and the fluids and gases aspirated, the inflatable member is deflated and the apparatus is removed from the interior of the placed chest tube.

23 Claims, 2 Drawing Sheets

Related U.S. Application Data

(60) Provisional application No. 61/735,230, filed on Dec. 10, 2012.

(51) Int. Cl.
| | | |
|---|---|---|
| *A61B 17/34* | (2006.01) | |
| *A61B 1/04* | (2006.01) | |
| *A61B 1/015* | (2006.01) | |
| *A61B 1/313* | (2006.01) | |
| *A61M 39/02* | (2006.01) | |
| *A61B 34/20* | (2016.01) | |
| *A61B 90/30* | (2016.01) | |

(52) U.S. Cl.
CPC ... *A61B 2217/005* (2013.01); *A61B 2217/007* (2013.01); *A61M 2039/0252* (2013.01); *A61M 2039/0261* (2013.01)

(56) References Cited

U.S. PATENT DOCUMENTS

| | | | | |
|---|---|---|---|---|
| 6,318,368 B1* | 11/2001 | Morejon | ............ | A61M 1/0078 128/207.15 |
| 6,461,294 B1* | 10/2002 | Oneda | ............ | A61B 1/00082 600/116 |
| 2002/0022769 A1* | 2/2002 | Smith | ............ | A61B 1/00052 600/188 |
| 2003/0195545 A1* | 10/2003 | Hermann | ............ | A61B 17/00008 606/191 |
| 2004/0186378 A1* | 9/2004 | Gesswein | ............ | A61M 25/0105 600/435 |
| 2005/0182297 A1* | 8/2005 | Gravenstein | ............ | A61B 1/0017 600/139 |
| 2007/0005041 A1* | 1/2007 | Frassica | ............ | A61M 25/0017 604/544 |
| 2007/0073343 A1* | 3/2007 | Jahns | ............ | A61B 17/0482 606/232 |
| 2009/0054805 A1* | 2/2009 | Boyle, Jr. | ............ | A61B 10/0266 600/564 |
| 2010/0063356 A1* | 3/2010 | Smith | ............ | A61B 1/3132 600/114 |
| 2012/0071721 A1* | 3/2012 | Remijan | ............ | A61B 1/00135 600/121 |
| 2013/0023729 A1* | 1/2013 | Vazales | ............ | A61B 1/0669 600/104 |

* cited by examiner

VIDEO-GUIDED CHEST TUBE INSERTION SYSTEM

CROSS-REFERENCE TO RELATED APPLICATIONS

This application is a 35 U.S.C. § 111(a) continuation of PCT international application number PCT/US2013/074213 filed on Dec. 10, 2013, incorporated herein by reference in its entirety, which claims priority to, and the benefit of, U.S. provisional patent application Ser. No. 61/735,230 filed on Dec. 10, 2012, incorporated herein by reference in its entirety. Priority is claimed to each of the foregoing applications.

The above-referenced PCT international application was published as PCT International Publication No. WO 2014/093401 on Jun. 19, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND OF THE INVENTION

1. Field of the Invention

This invention pertains generally to medical insertion devices, and more particularly to a flexible chest tube insertion apparatus with a hardened insertion tip, video camera, fluid lumen and stiffening balloon that is inserted within the chest tube and expanded during use.

2. Description of Related Art

The inside of the mammalian chest cavity is lined with two layers of pleural tissue (visceral and parietal) that are separated by the pleural space. The interior of the chest is kept at a negative pressure to keep the lungs inflated. The presence of air in the pleural space (pneumothorax), blood in the pleural space (hemothorax) or fluid (pleural effusion) are commonly occurring conditions arising from chest trauma, diseases or surgical procedures that can be potentially lethal without prompt treatment.

Chest tubes are typically placed into the pleural space of patients who have air and/or fluid around the lung that can collapse the lung. The chest tube is normally placed more anteriorly around the second or third intercostal space (ICS) in the anterior axillary or midclavicular line when air is the expected product to be drained. When blood or fluid is to be drained, the tube is typically inserted around the fifth to seventh ICS.

A conventional chest tube is usually a pre-packaged sterile plastic tube with a central metal trochar. These tubes currently are placed in the body either by making a surgical incision between adjacent ribs and making a hole into the chest crudely with a clamp or by a "Seldinger" technique which is to place a wire in the chest and then blindly pass dilators over the wire until the tube can be inserted into the opened space.

However, surgical dissection through the chest wall can result in complications. For example, over penetration during insertion can puncture major organs such as the lungs, liver, heart and spleen as well as produce vascular system injuries, diaphragm perforation and insertion site infections. These methods can produce problems with excessive pain as well as poor tube positioning since there is no visual feedback as to the location of the tubes during insertion thereby leading to unnecessary risks for patients.

Accordingly, there is a need for a chest tube insertion system and apparatus that will allow accurate placement of the chest tube while avoiding internal injuries and complications from the insertion procedure. The present invention satisfies that need as well as others and is generally an advancement in the art.

BRIEF SUMMARY OF THE INVENTION

The present invention is a chest tube placement system that is disposed within the bore of a conventional chest tube for insertion into a patient. The apparatus has an elongate body with associated leads and tubes that are preferably enclosed in a sterile plastic sleeve/bag.

The exterior of the body has at least one inflatable member attached to a source of air or liquid that inflates or deflates the inflatable member within the chest tube creating rigidity in the chest tube during insertion when the member is inflated.

The body also has a hard tip that is shaped to facilitate insertion through the intercostal space to the plural cavity. The tip may be threaded to assist in the insertion through the chest wall. The tip has an injection/aspiration port connected to an axial channel in the body and a tube that permits the expulsion of material such as anesthetic or antibiotics from the tip as well as the withdrawal of material by creating a negative pressure in the tube. In another embodiment, separate ports and channels for injection and aspiration are used.

The body of the apparatus also has a video camera and light that is attached to a display that allows a physician to easily place a chest tube into the pleural space under direct vision to confirm the location of the tip and the condition of the pleural space. The physician can simultaneously visualize the local anatomy and provide directed anesthetic coverage to the area of insertion and then evacuate fluid and/or air from the pleural space, all in a sterile enclosed system.

According to one aspect of the invention, a chest tube placement system and apparatus is provided that uses a video source so that the placement of the tube is accomplished under real time visualization of the tip location and actual control of insertion by having a controlled directional "scope" so that tube insertion injuries can be avoided.

Another aspect of the invention is to provide a chest tube placement system that has a sterile sleeve or bag so that the video camera, light source and leads do not themselves need to be sterilized.

According to another aspect of the invention, a chest tube placement apparatus is provided that has a port at the end of the tip of the body for localized injection of anesthetic agents for adequate local anesthesia.

A further aspect of the invention is to provide a chest tube placement apparatus that has a suction channel to remove fluid and/or air directly and optimally from the pleural cavity while placing the chest tube.

Still another aspect the invention is to provide a chest tube placement apparatus that has a balloon that "expands" the size of the body portion of the device so that it will fit tightly into any size chest tube, preferably from about 20 French to 36 French, to provide rigidity during initial insertion but also flexibility (by deflating slightly) when "steering" the tube with the video device to allow optimal chest tube placement.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
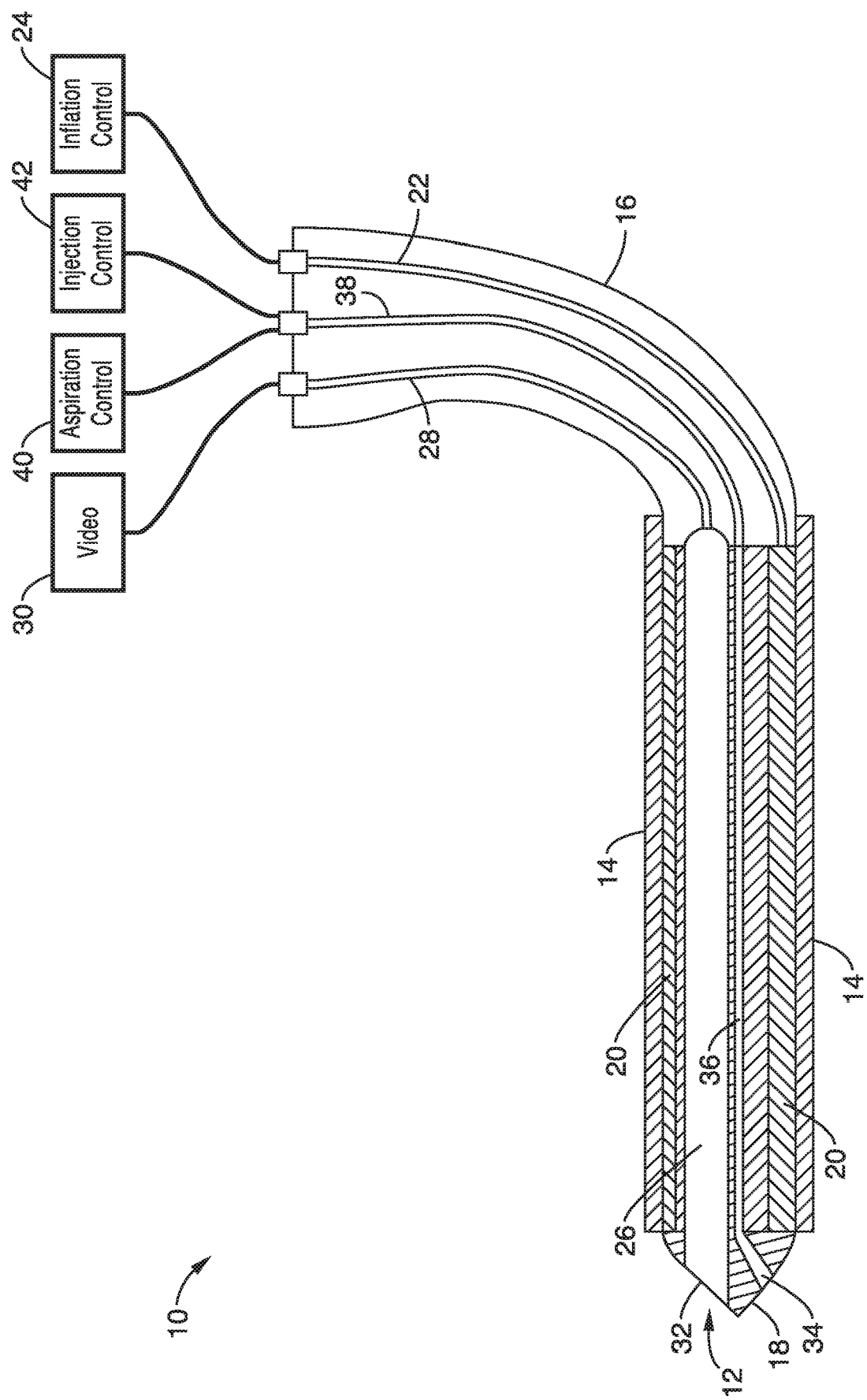
FIG. 1 is a schematic cross-sectional side view of one embodiment of the chest tube insertion apparatus disposed within a chest tube according to the invention.
Figure 2:
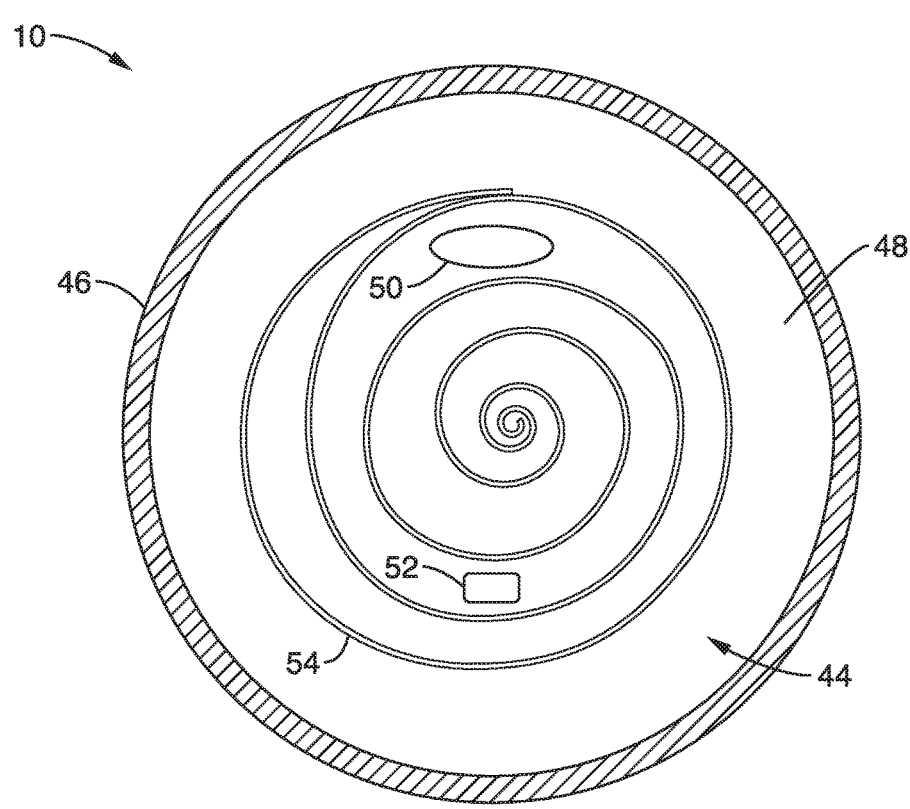
FIG. 2 is a front end view of the apparatus showing one embodiment of the insertion tip and expanded body within a chest tube according to the invention.

Referring more specifically to the drawings, for illustrative purposes, an embodiment of the chest tube apparatus of the present invention is depicted generally in FIG. 1 and FIG. 2. It will be appreciated that the methods of use may vary as to the specific steps and sequence and the apparatus may vary as to structural details, without departing from the basic concepts as disclosed herein.

Turning now to FIG. 1, a cross-sectional side view of one embodiment of the chest tube insertion apparatus 10 disposed in a chest tube is schematically shown. The chest tube insertion apparatus 10 has a body 12 that is inserted into a conventional chest tube 14. Chest tubes in the art come in different sizes. However, the preferred size of the body 12 is a single size that can be used with variable chest tube sizes at least from about 20 French to about 36 French.

A sterile bag or sleeve 16 is preferably connected to at least the distal end of the body 12 to enclose the leads and lines and create a sterile enclosure so that the individual leads and lines do not need to be sterilized. In one embodiment, the body 12, as well as the lines, is enclosed in the sterile sleeve 16.

The body 12 is generally cylindrical with a tip 18 on the proximal end that preferably has a pointed shape or a tapered "blade-like" end that can facilitate passage of the apparatus through tissues and chest wall of the patient. However, the body 12 may also be tapered to fit within a tapered chest tube in one embodiment. The body 12 is preferably semi-rigid and rigid at the tip end but may be otherwise have some flexibility.

An inflatable member 20 is mounted to the exterior of the body 12 that engages the interior of the chest tube 14 upon inflation firmly securing the chest tube to the body 12. The inflatable member 20 is preferably mounted circumferentially to the cylindrical body 12 so that the diameter of the apparatus increases equally upon inflation. However, in one embodiment, several inflatable members are used. In another embodiment, only a single inflatable member is used so that both the inflatable member 20 and the exterior surface of the body 12 engage the interior of the chest tube 14.

The inflatable member 20 is coupled to a fluid line 22 that directs air or liquid into or out of the member 20 to inflate or deflate the inflatable member 20. An inflation control 24 provides and controls the movement of fluid into or out of the inflatable member 20. Inflation control 24 includes a source of compressed air or liquid from a source such as a mechanical pump, a container of compressed air or a hand pump along with control valves to allow control over the extent of inflation and deflation of inflatable member 20. Inflation of the inflatable member 20 when the body 12 of the apparatus is disposed in a chest tube 14 creates a rigid combination that can be inserted in the site that has been prepared for the chest tube 14.

The body 12 also has a video camera 26 with an appropriate lighting source so that the progress of the chest tube-apparatus and the location of organs and other structures can be monitored so that over penetration, organ perforation and improper positioning can be avoided. In one embodiment, a fiber optic cable is used as a light source adjacent to the video camera.

The video camera 26 is coupled to a display and video control 30 with a control lead cable 28 to allow real time viewing of the surroundings of the tip 18 of apparatus during insertion and placement. In the embodiment shown in FIG. 1, the tip 18 has a viewing port 32 to allow the video camera 26 to view the immediate surroundings of the front tip 18. In an alternative embodiment, the imaging device is a standard bronchoscope that can pass down the inside of the body 12 to the tip 18 that has a "window" 32 that the video imaging device of the scope fits into in order to visualize the tissue and space around the end of the chest tube.

Tip 18 also has an injection/aspiration port 34 that is connected to an axial channel 36 through the body 12 and a delivery tube 38 in the embodiment shown in FIG. 1. The delivery tube 38 is coupled to an aspiration control 40 and injection control 42 that control the injection of material out of port 34 and the aspiration of material into port 34 and out through channel 36 and line 38. The material that is injected is typically a local anesthetic agent to reduce pain or a vasoconstrictor to temporarily control bleeding at the insertion site. In one embodiment, the injection control 42 is a sterile syringe injection point so that the system is closed and the anesthesia is delivered by injection by a syringe and the amount of injected material can be monitored.

Suction of air and/or fluid from the pleural space at the time of insertion can be accomplished by reducing the pressure in line 38 and channel 36 so that gases or liquids surrounding tip 18 are drawn in through port 34 and ultimately removed from the system. Aspiration control 40 can be a valve coupled to a syringe or a vacuum pump and valves for creating a negative pressure in the lines. Traps can also be included with aspiration control 40 to collect aspirated waste.

Although the embodiment shown in FIG. 1 has a single channel 36 and line 38 that is shared between injection and aspiration functions, it will be understood that separate suction and injection channels and suction and injection lines and ports can also be used. A single shared channel and port is preferred because the delivery of anesthetic and the aspiration of gasses and fluids can be performed sequentially.

The tip 18 of body 12 can be conical or wedge shaped to assist in the placement of the chest tube through the chest wall. In the embodiment shown in FIG. 2, the tip 44 is generally conical and has a set of exterior threads 54. The apparatus has been placed in a chest tube 46 and the inflatable member 48 has been inflated to fully engage the interior of the chest tube 46 and is ready for insertion into the body of a patient. The view port 50 allows the video source with a light to help visualize directly the anatomy of the patient during insertion of the chest tube. A port 52 is also present in the tip 44 to allow the injection and aspiration of material through the tip 44.

In use, the size of the chest tube to be installed and the location of its placement are determined by the physician. A typical location for an incision is at the fourth or fifth intercostal space. The area of insertion is normally prepared with an application of a local anesthetic and an antiseptic.

The apparatus is inserted into the interior of the selected chest tube tip first and positioned so that the tip is beyond the end of the chest tube. The leads connected to the body are enclosed within the sterile sleeve on the opposite end of the body from the tip. The leads and lines that are within the sleeve are coupled to the video display and injection and aspiration control features.

The inflatable member is inflated with air produced by a hand pump or other source of compressed air or liquid. Inflation "stiffens" the chest tube to make it rigid and strong enough to pierce the chest wall. Anesthetic is injected into the apparatus and delivered to the injection/aspiration port at the tip and the video camera is actuated. The apparatus is now ready for insertion.

The apparatus is inserted tip first through the dissected site and positioned within the pleural cavity using the video images on the display to steer the apparatus. Aspiration of the residual anesthetic and fluids typically occurs after placement of the apparatus and tube at the proper position in the body. The aspiration of air or fluids at the site can be conducted at the time of placement with the apparatus. Once properly placed, the inflatable member is deflated and the apparatus is removed from the interior of the chest tube. The tube normally remains in the chest of the patient until all or most of the air or fluid has been drained out, which usually takes a few days.

From the discussion above it will be appreciated that the invention can be embodied in various ways, including the following:

1. A chest tube placement apparatus, comprising: an elongate body with a rigid tip configured for insertion into a flexible chest tube having a hollow interior; and at least one inflatable member coupled to an exterior surface of the elongate body; the inflatable member having a first expanded position that stiffens the chest tube and a second unexpanded position that restores flexibility to the chest tube.

2. An apparatus as recited in any previous embodiment, wherein the tip of the elongate body has a conical shape with external threads.

3. An apparatus as recited in any previous embodiment, further comprising: a video camera disposed within the elongate body; and a display monitor; wherein video images from the video camera are displayed on the display monitor; and wherein the position of the chest tube and internal structures within the body of a patient during insertion can be monitored.

4. An apparatus as recited in any previous embodiment, the elongate body further comprising: a plurality of lights, the lights emitting light rays from the tip of the elongate body.

5. An apparatus as recited in any previous embodiment, the elongate body further comprising: an axial injection channel with a tip injection port and an input port; and a tubular injection line coupled to the input port; wherein fluids introduced to the injection line are ejected through the tip injection port.

6. An apparatus as recited in any previous embodiment, the elongate body further comprising: an axial aspiration channel with a tip intake port and an output port; a vacuum pump; and an aspiration vacuum line coupled to the output port and the vacuum pump; wherein gases and fluids are aspirated through the intake port upon actuation of the vacuum pump.

7. A chest tube placement apparatus, comprising: an elongate body with a rigid tip configured for insertion into a flexible chest tube having a hollow interior; a video camera disposed within the elongate body coupled to a display monitor by a video lead; and a circumferential inflatable member coupled to an exterior surface of the elongate body; the inflatable member having a first expanded position that stiffens a chest tube and a second unexpanded position that restores flexibility to the chest tube; wherein video images from the video camera are displayed on the display monitor; and wherein position of the chest tube and internal structures within the body of a patient during insertion can be monitored.

8. An apparatus as recited in any previous embodiment, the elongate body further comprising: a plurality of lights, the lights emitting light rays from the tip of the elongate body.

9. An apparatus as recited in any previous embodiment, the elongate body further comprising: an axial injection channel with a tip injection port and an input port; and a tubular injection line coupled to the input port; wherein fluids introduced to the injection line are ejected through the tip injection port.

10. An apparatus as recited in any previous embodiment, the elongate body further comprising: an axial aspiration channel with a tip intake port and an output port; a vacuum pump; and an aspiration vacuum line coupled to the output port and the vacuum pump; wherein gases and fluids are aspirated through the intake port upon actuation of the vacuum pump.

11. An apparatus as recited in any previous embodiment, the elongate body further comprising: a sterile flexible sleeve mounted to the elongate body, the sleeve enclosing the video lead.

12. An apparatus as recited in any previous embodiment, wherein the tip of the elongate body has a conical shape with exterior threads.

13. An apparatus as recited in any previous embodiment, further comprising: a flexible chest tube having a hollow interior, the elongate body disposed in the hollow interior of the flexible chest tube.

14. A chest tube placement apparatus, comprising: an elongate body with a rigid tip and an axial material transfer channel coupled to a tubular material transfer lead and a tip port; a video camera disposed within the elongate body coupled to a display monitor by a video lead; a circumferential inflatable member mounted to an exterior surface of the elongate body and coupled to a tubular inflation lead and source of compressed air; and a sterile sleeve coupled to the elongate body, the sterile sleeve enclosing the material transfer lead, video lead and inflation lead; wherein the inflatable member has a first expanded position that stiffens a chest tube when inserted into a hollow interior of a chest tube and a second unexpanded position that restores flexibility to the chest tube; wherein video images from the video camera are displayed on the display monitor; and wherein a position of the chest tube and internal structures within the body of a patient during insertion can be monitored.

15. An apparatus as recited in any previous embodiment, further comprising: a flexible chest tube having a hollow interior, the elongate body disposed in the hollow interior of the flexible chest tube.

16. An apparatus as recited in any previous embodiment, the elongate body further comprising: a plurality of lights, the lights emitting light rays from the tip of the elongate body.

17. An apparatus as recited in any previous embodiment, wherein the source of compressed air is selected from the group consisting of a hand pump, a mechanical pump and a container of compressed air.

18. An apparatus as recited in any previous embodiment, further comprising: a vacuum pump; and a control valve joined to the material transfer lead; wherein actuation of the vacuum pump and valve allow aspiration of gases or liquids into the tip port for removal.

19. An apparatus as recited in any previous embodiment, further comprising: an injection port coupled to the material transfer lead, wherein injection of a material into the injection port is ejected at the tip of the elongated body through the tip port.

20. An apparatus as recited in any previous embodiment, further comprising: a control valve joined to the material transfer lead; a vacuum pump coupled to the control valve; and an injection port coupled to the control valve; wherein actuation of the vacuum pump and control valve allow aspiration of gases or liquids into the tip port for removal; and wherein injection of a material into the injection port is ejected at the tip of the elongated body through the d tip port.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A chest tube placement apparatus, comprising:
an elongate body comprising a distal end and a proximal end, with a rigid tip at the distal end and configured for insertion into a flexible chest tube having a hollow interior; and
an inflatable member coupled to an exterior surface of the elongate body and extending along at least an axial section of the elongate body from a distal location at the rigid tip to a proximal location toward the proximal end of the elongate body;
wherein when said elongate body and said inflatable member are inserted into the chest tube, the inflatable member is disposed in an annular gap extending at least along said axial section between the exterior surface of the elongate body and an interior wall of the chest tube such that expansion of the inflatable member engages an axial length of the interior wall of the chest tube, the axial length of the interior wall extending from a distal end of the flexible chest tube and corresponding to the length of the axial section;
the inflatable member having a first expanded position that engages the interior wall of the chest tube to couple the elongate body to the chest tube and to stiffen the chest tube along said axial length and a second unexpanded position that decouples the elongate body from the chest tube and restores flexibility to the chest tube;
wherein the elongate body and the inflatable member are configured for insertion into the chest tube in the unexpanded position;
wherein when the inflatable member is in the expanded position after insertion into the chest tube, the combination of the elongate body, the inflatable member and the chest tube operate in concert for insertion of the chest tube through a chest wall of a patient; and
wherein when the inflatable member is in the unexpanded position after the chest tube is inserted through the chest wall of the patient, the elongate body and the inflatable member are configured for removal from the chest tube while the chest tube remains in place.

2. An apparatus as recited in claim 1, wherein said tip of said elongate body has a conical shaped surface with external threads extending along the conical shaped surface.

3. An apparatus as recited in claim 1, further comprising:
a video camera disposed within said elongate body; and
a display monitor;
wherein video images from said video camera are displayed on the display monitor; and
wherein position of the chest tube and internal structures within the body of a patient during insertion can be monitored.

4. An apparatus as recited in claim 3, said elongate body further comprising:
a plurality of lights, said lights emitting light rays from the tip of the elongate body.

5. An apparatus as recited in claim 1, said elongate body further comprising:
an axial injection channel with a tip injection port and an input port; and
a tubular injection line coupled to the input port;
wherein fluids introduced to the injection line are ejected through the tip injection port.

6. An apparatus as recited in claim 1, said elongate body further comprising:
an axial aspiration channel with a tip intake port and an output port;
a vacuum pump; and
an aspiration vacuum line coupled to the output port and the vacuum pump;
wherein gases and fluids are aspirated through the intake port upon actuation of the vacuum pump.

7. The apparatus of claim 1, wherein the rigid tip of the elongate body comprises a sharpened profile at the distal end; and
wherein when the inflatable member is in the expanded position, the rigid distal tip of the elongate body extends outside of and distal to the distal end of the flexible chest tube to promote piercing through a chest wall tissue of the patient.

8. A chest tube placement apparatus, comprising:
an elongate body comprising a distal end and a proximal end, with a rigid tip at the distal end and configured for insertion into a flexible chest tube having a hollow interior;
a circumferential inflatable member coupled to an exterior surface of the elongate body and extending along at least an axial section of the elongate body from a distal location at the rigid tip to a proximal location toward the proximal end of the elongate body;
wherein when the elongate body and the circumferential inflatable member are inserted into the chest tube, the circumferential inflatable member is disposed in an annular gap extending at least along said axial section between the exterior surface of the elongate body and an interior wall of the chest tube such that expansion of the circumferential inflatable member engages an axial length of the interior wall of the chest tube, the axial length of the interior wall extending from a distal end of the chest tube and corresponding to the length of the axial section;

the circumferential inflatable member having a first expanded position that engages the interior wall of the chest tube to couple the elongate body to the chest tube and to stiffen the chest tube along said axial length and a second unexpanded position that decouples the elongate body from the test tube and restores flexibility to the chest tube;

wherein the elongate body and the circumferential inflatable member are configured for insertion into the chest tube in the unexpanded position;

wherein when the circumferential inflatable member is in the expanded position after insertion into the chest tube, the combination of the elongate body, the inflatable member and the chest tube operate in concert for insertion of the chest tube through a chest wall of a patient; and wherein when the circumferential inflatable member is in the unexpanded position after the chest tube is inserted through the chest wall of the patient, the elongate body and the circumferential inflatable member are configured for removal from the chest tube while the chest tube remains in place.

9. An apparatus as recited in claim 8, said elongate body further comprising:
a plurality of lights, said lights emitting light rays from the tip of the elongate body.

10. An apparatus as recited in claim 8, said elongate body further comprising:
an axial injection channel with a tip injection port and an input port; and
a tubular injection line coupled to the input port;
wherein fluids introduced to the injection line are ejected through the tip injection port.

11. An apparatus as recited in claim 8, said elongate body further comprising:
an axial aspiration channel with a tip intake port and an output port;
a vacuum pump; and
an aspiration vacuum line coupled to the output port and the vacuum pump;
wherein gases and fluids are aspirated through the intake port upon actuation of the vacuum pump.

12. An apparatus as recited in claim 8, further comprising:
a video camera disposed within said elongate body coupled to a display monitor by a video lead, wherein video images from said video camera are displayed on the display monitor;
wherein position of the chest tube and internal structures within the body of a patient during insertion can be monitored; and
a sterile flexible sleeve mounted to the elongate body, the sleeve enclosing the video lead.

13. An apparatus as recited in claim 8, wherein said tip of said elongate body has a conical shaped surface with external threads extending along the conical shaped surface.

14. An apparatus as recited in claim 8,
wherein a diameter of the circumferential inflatable member increases equally upon inflation to circumferentially engage said flexible chest tube at said interior wall of said hollow interior, said combination of the elongate body, the circumferential inflatable member in the expanded configuration and the flexible chest tube operating in concert to form a rigid structure at the distal end of the flexible chest tube for insertion of the chest tube through the chest wall of the patient.

15. The apparatus of claim 8, wherein the rigid tip of the elongate body comprises a sharpened profile at the distal end; and
wherein when the circumferential inflatable member is in the expanded position, the rigid distal tip of the elongate body extends outside of and distal to a distal end of the flexible chest tube such that the combination of the elongate body, the circumferential inflatable member and the flexible chest tube operate in concert to form a rigid structure at the distal end of the flexible chest tube to promote piercing of a chest wall tissue for insertion of the chest tube through the chest wall of the patient.

16. A chest tube placement apparatus, comprising:
a flexible chest tube having a hollow interior defined by an interior wall;
an elongate body comprising a distal end and a proximal end and sized for insertion within the flexible chest tube, the elongate body having a rigid tip with a sharpened profile at the distal end to promote piercing through a chest wall tissue of the patient;
a circumferential inflatable member mounted to an exterior surface of the elongate body and extending along at least an axial section of the elongate member from a distal location at the rigid tip to a proximal location toward the proximal end of the elongate body and coupled to a tubular inflation lead and source of compressed air; and
wherein when said elongate body and said circumferential inflatable member are inserted into the chest tube, the circumferential inflatable member is disposed in an annular gap extending at least along said axial section between the exterior surface of the elongate body and an interior wall of the chest tube such that expansion of the circumferential inflatable member engages an axial length of the interior wall of the chest tube, the axial length of the interior wall corresponding to the length of the axial section;
wherein the circumferential inflatable member has a first expanded position that that engages the interior wall of the chest tube to couple the elongate body to the chest tube and to stiffen the chest tube along said axial length and a second unexpanded position that decouples the elongate body from the chest tube and restores flexibility to the chest tube;
wherein the elongate body and the circumferential inflatable member are configured for insertion into the chest tube in the unexpanded position;
wherein when the inflatable member is in the expanded position after insertion into the chest tube, the rigid distal tip of the elongate body extends outside of and distal to a distal end of the chest tube and the combination of the elongate body, the circumferential inflatable member and the chest tube operate in concert to form a rigid structure at the distal end of the chest tube for insertion of the chest tube through a chest wall of a patient; and
wherein when the circumferential inflatable member is in the unexpanded position after the chest tube is inserted through the chest wall of the patient, the elongate body and circumferential inflatable member are configured for removal from the chest tube while the chest tube remains in place.

17. An apparatus as recited in claim 16, wherein a diameter of the circumferential inflatable member increases equally upon inflation to circumferentially engage said flexible chest tube at said interior wall of said hollow interior.

18. An apparatus as recited in claim 16, said elongate body further comprising:
a plurality of lights, said lights emitting light rays from the tip of the elongate body.

19. An apparatus as recited in claim 16, wherein said source of compressed air is selected from the group consisting of a hand pump, a mechanical pump and a container of compressed air.

20. An apparatus as recited in claim 16, further comprising:
a vacuum pump; and
a control valve joined to the material transfer lead;
wherein actuation of the vacuum pump and valve allow aspiration of gases or liquids into the tip port for removal.

21. An apparatus as recited in claim 16, further comprising:
an injection port coupled to the material transfer lead,
wherein injection of a material into the injection port is ejected at said tip of the elongated body through said tip port.

22. An apparatus as recited in claim 16, further comprising:
a control valve joined to the material transfer lead;
a vacuum pump coupled to the control valve; and
an injection port coupled to the control valve;
wherein actuation of the vacuum pump and control valve allow aspiration of gases or liquids into the tip port for removal; and
wherein injection of a material into the injection port is ejected at said tip of the elongated body through said tip port.

23. The apparatus of claim 16, wherein the axial length of the interior wall extends from the distal end of the flexible chest tube.

* * * * *